US006663588B2

(12) United States Patent
DuBois et al.

(10) Patent No.: US 6,663,588 B2
(45) Date of Patent: Dec. 16, 2003

(54) ACTIVE COUNTERFORCE HANDLE FOR USE IN BIDIRECTIONAL DEFLECTABLE TIP INSTRUMENTS

(75) Inventors: Tom DuBois, Glens Falls, NY (US); Mark Eberhardt, Glens Falls, NY (US); Frank Madia, Queensbury, NY (US)

(73) Assignee: C.R. Bard, Inc., Murray Hill, NJ (US)

( * ) Notice: Subject to any disclaimer, the term of this patent is extended or adjusted under 35 U.S.C. 154(b) by 86 days.

(21) Appl. No.: 09/725,606

(22) Filed: Nov. 29, 2000

(65) Prior Publication Data

US 2002/0065485 A1 May 30, 2002

(51) Int. Cl.[7] ............................................. A61M 37/00
(52) U.S. Cl. ................... 604/95.04; 604/95.01
(58) Field of Search ................ 604/95.01, 95.02, 604/95.04, 95.05, 93.01, 5.23, 528–532, 264; 600/588, 434, 121; 606/194, 108, 192, 191

(56) References Cited

U.S. PATENT DOCUMENTS

| | | | |
|---|---|---|---|
| 5,190,050 A | 3/1993 | Nitzsche | 128/772 |
| 5,318,525 A | 6/1994 | West et al. | 604/95 |
| 5,383,852 A | 1/1995 | Stevens-Wright | 604/95 |
| 5,549,542 A | 8/1996 | Kovalcheck | 600/146 |
| 5,611,777 A | 3/1997 | Bowden et al. | 604/95 |
| 5,681,280 A | 10/1997 | Rusk et al. | 604/95 |
| 5,741,320 A | 4/1998 | Thorton et al. | 607/122 |
| 5,861,024 A | 1/1999 | Rashidi | 607/122 |
| 5,904,667 A | 5/1999 | Falwell | 604/95 |
| 5,944,690 A * | 8/1999 | Falwell et al. | 604/95 |
| 6,007,531 A | 12/1999 | Snoke et al. | 606/15 |
| 6,013,052 A | 1/2000 | Durman et al. | 604/95 |
| 6,464,645 B1 * | 10/2002 | Park et al. | 600/462 |

* cited by examiner

Primary Examiner—Long V. Le
Assistant Examiner—Ann Y. Lam
(74) Attorney, Agent, or Firm—Darby & Darby

(57) ABSTRACT

The present invention is directed to an active handle assembly for use in a bidirectional steerable surgical instrument having a deflectable distal end. Typically, the surgical instrument includes a handle component which the user manipulates to cause a distal end of the instrument to deflect. The distal end comprises an end tip portion of a shaft which extends outwardly from the handle. A control mechanism is disposed within the handle and extends through the shaft for selectively controlling the direction and degree of deflection at the distal end. For example, one exemplary control mechanism uses control or steering wires to deflect the distal end. The active counterforce mechanism according to the present invention is designed to be used in combination with the control mechanism and provides a force which counters the return to center force generated by the deflection of the shaft at the distal end thereof. Optimally, the active counterforce mechanism balances the return to center force across the instrument's deflection range in distal and proximal directions. This results in the user experiencing minimal, if any, resistance during the manual manipulation of the control mechanism.

7 Claims, 4 Drawing Sheets

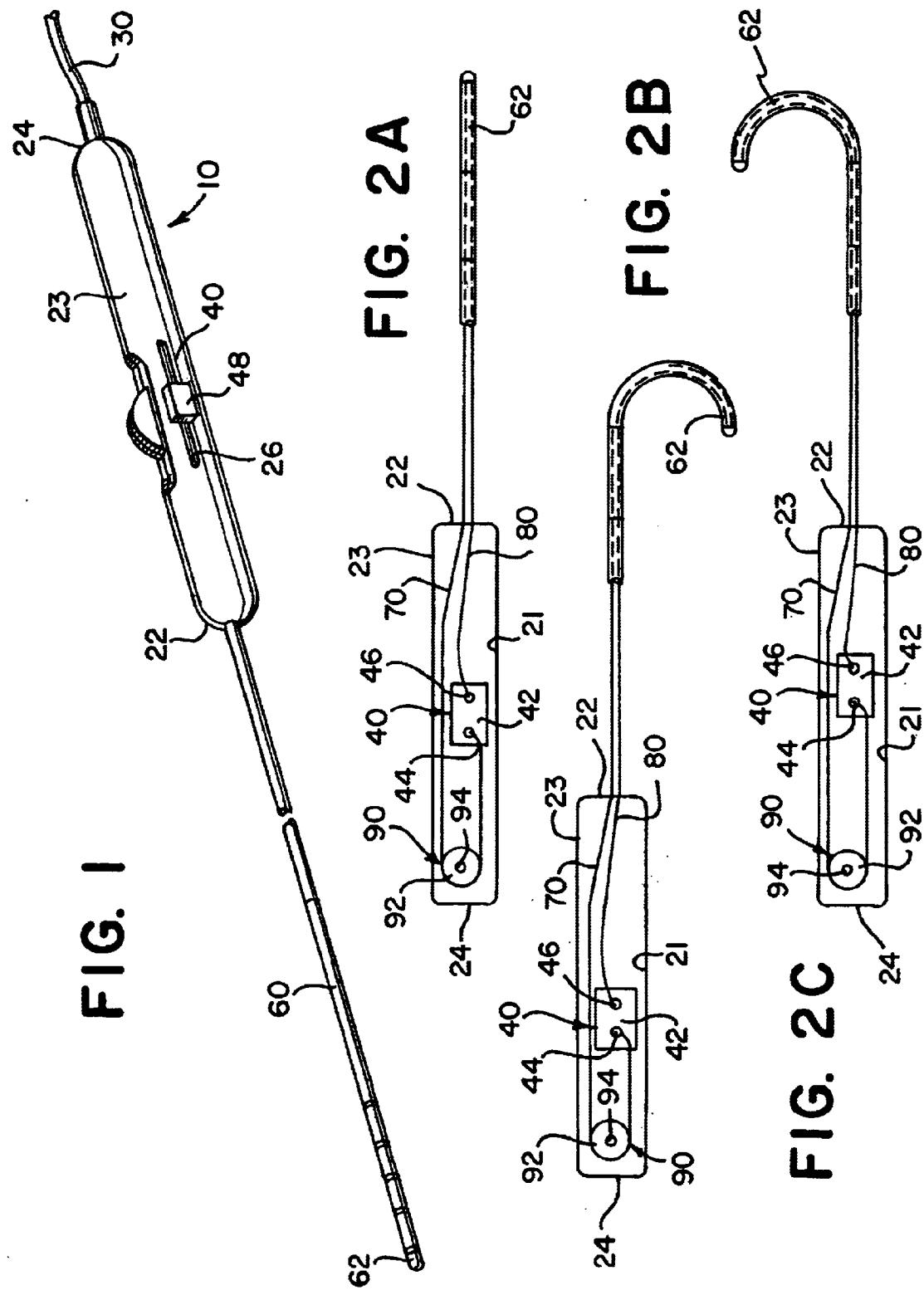

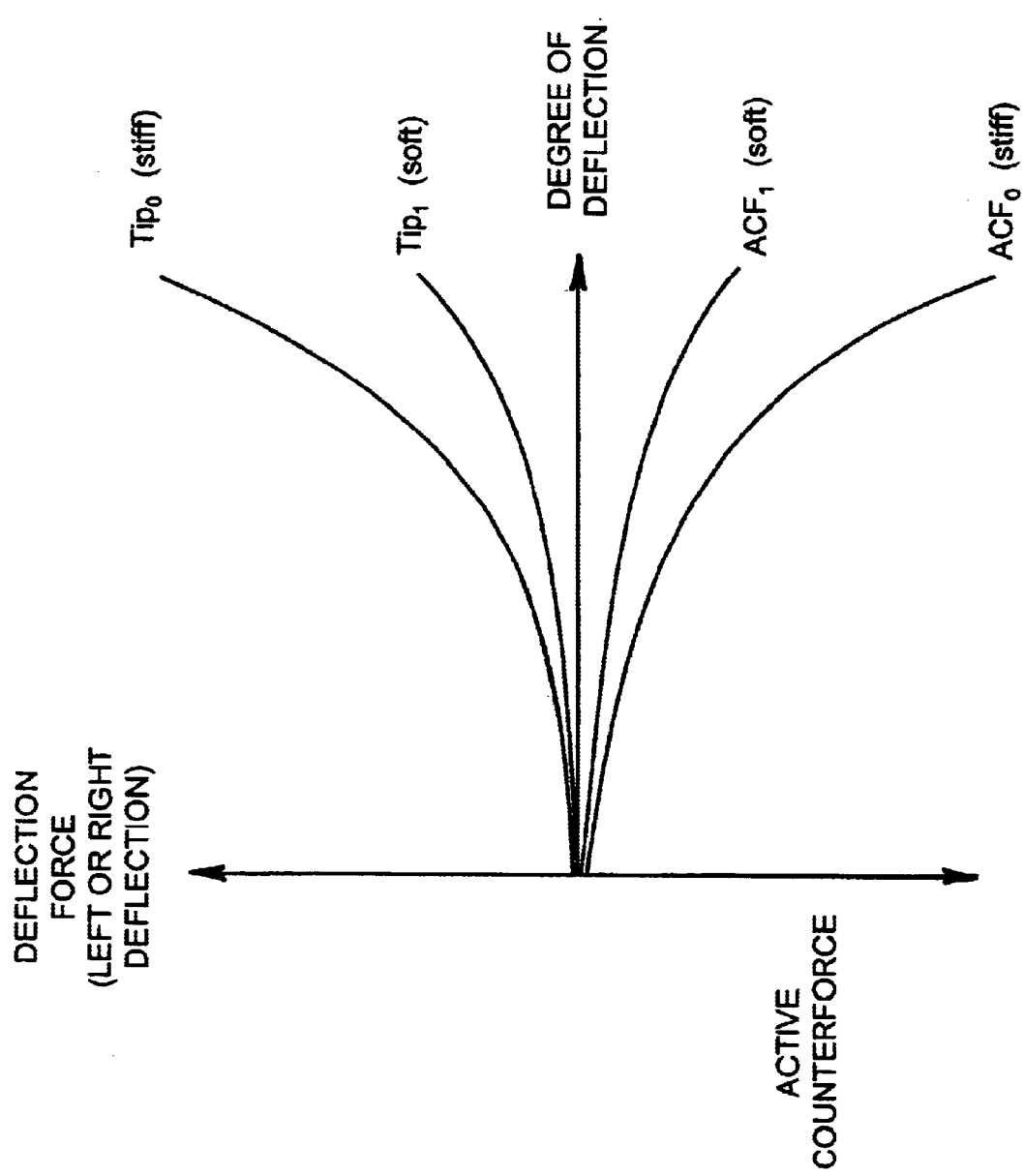

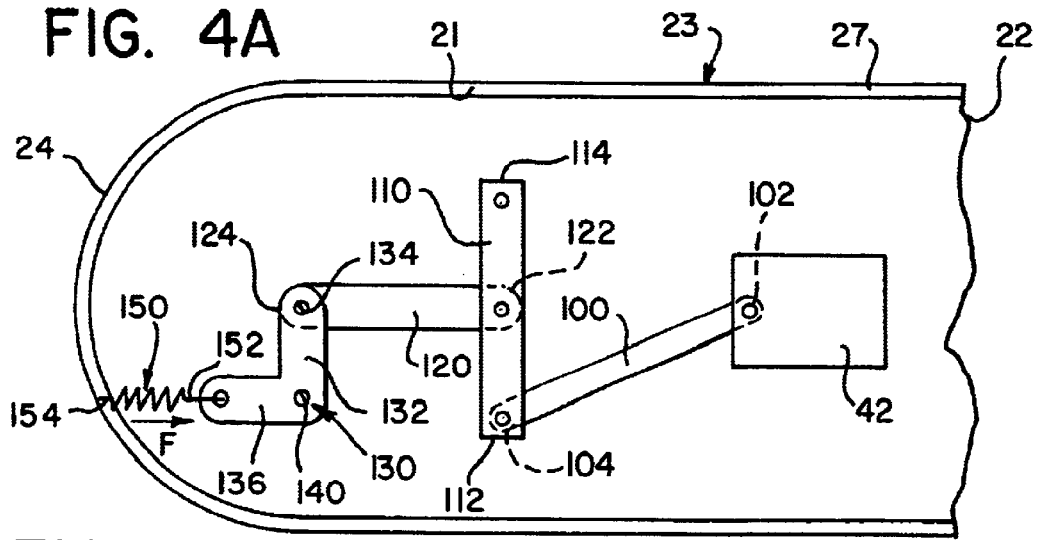
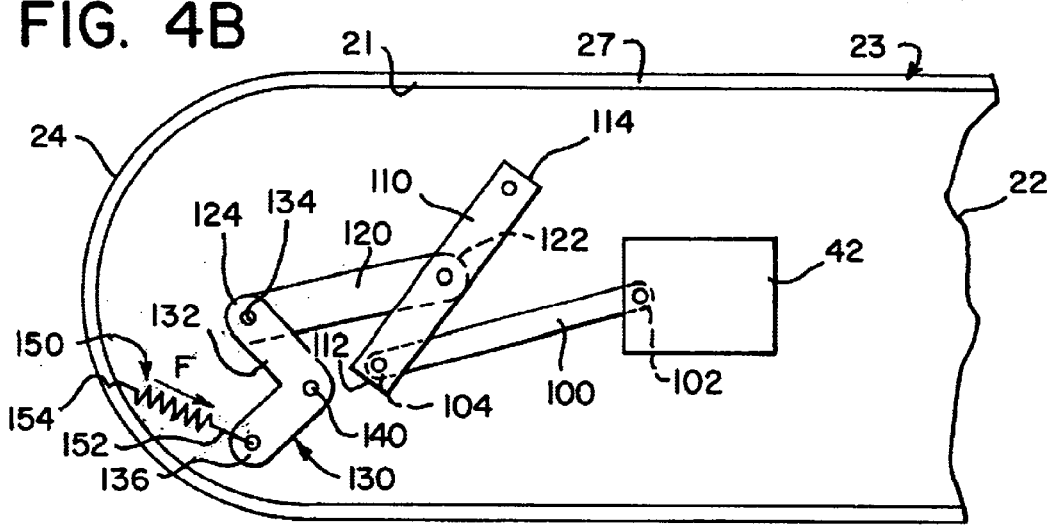
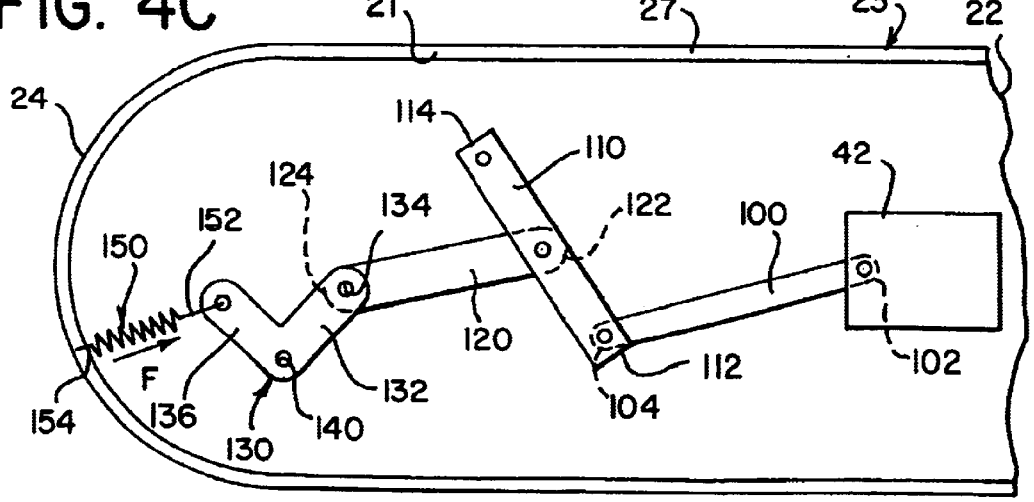

ACTIVE COUNTERFORCE HANDLE FOR USE IN BIDIRECTIONAL DEFLECTABLE TIP INSTRUMENTS

FIELD OF THE INVENTION

This invention relates to the field of deflectable tip instruments and, more particularly, to an active counterforce handle for use in such instruments to counter a return to center force generated by an instrument shaft upon being deflected.

BACKGROUND OF THE INVENTION

Modern surgical procedures often necessitate localized diagnosis, or treatments applied to relatively inaccessible interior areas of the body. In the past, such procedures have typically involved invasive surgery, enabling the physician to visually identify or treat the area of interest by accessing a relatively large opening or incision made in the body. Unfortunately, invasive surgical methods often include undesirable side-effects, from the tissue trauma associated with the procedure. Often, the effects of the trauma prolong the healing and rehabilitation period for the patient.

To minimize the trauma often associated with invasive surgery, those skilled in the art have developed relatively small surgical instrument, such as catheters, for insertion into the vasculature of the body. Typically, the particular surgical instrument accesses the body through a small incision made near the skin, where it can then be advanced to an area of interest. However, in order to navigate through the vasculature in a predictable manner, the instrument must be precisely controllable to position, as examples, ablation electrodes or imaging probes proximate specific tissues of interest.

To enable manipulation of the instrument, such as a catheter, inside the body, a number of mechanism may be used to selectively "steer" the distal tip of the catheter while the operator inserts the device into the body. One such mechanism is a slidable control wire mechanism which includes a pair of control wires that span the length of the catheter shaft, or body. The control wires have respective distal ends anchored to specific locations at the distal tip of the catheter body corresponding to predetermined deflectional movement. The proximal ends of the wires are mounted to a slider mechanism that responds to the operator by placing one of the wires in tension, pulling at the catheter end for deflection in a first direction, while simultaneously compressing, or buckling, the other wire. An example of such a catheter configuration incorporating such a control mechanism is found in U.S. Pat. No. 5,383,852, assigned to the assignee of the present invention, and herein incorporated by reference in its entirety.

Typically, the surgical instrument includes a handle component. Handles for deflectable tip instruments typically rely on the user to generate the force required to deflect the tip member in either direction, to maintain deflection, and to return the tip member to center after deflection. Devices which accomplish the foregoing are often referred to as having bidirectional steering. Sometimes, the tip member is only deflected in one direction and is relied upon to generate the force required to return the tip member to center. These devices are referred to as having unidirectional. In all of these conventional handle designs, the handle is a passive component. The handle does not generate any force, it merely delivers the force applied by the user.

When the distal end of the instrument body, e.g. catheter body, is deflected, a force is generated that tends to drive the distal end back to its straightened position. This is commonly referred to as a "return to center" force. This is usually not a desired effect, for in use, it is often convenient for the user if once the catheter body is deflected, it remains so without the continuing input of force from the user to counter the return to center force coming from the catheter body. Existing passive instrument designs have needed to rely on friction, ratchets, or other "drag" mechanisms for producing this counter effect. For example, one such counter mechanism uses a set screw included within the handle to hold the catheter body in various locations so as to prevent the distal end of the catheter body from straightening out when the physician releases the handle. The set screw generally applies a friction force to the operational components of the handle. The friction force applied to the handle components must, of course, be greater than the maximum force generated by the distal end of the catheter body. The maximum force is generated when the distal end is in its most curved orientation. One of the associated disadvantages of such counter mechanisms is that in order to achieve the required drag to maintain the shape of the catheter body, the force required to deflect the distal end may be inconvenient to the user. In other words, it may be difficult for many users to conveniently use a thumb or finger to manipulate the handle to cause deflection of the distal end because the force required to do so is too great.

U.S. Pat. No. 6,013,052 ('052) to Durham et al. discloses a catheter handle having a piston-type actuator device along with a biasing element which biases the piston in the distal direction. The '052 patent is hereby incorporated by reference in its entirety. The device disclosed in the '052 patent is of the type which has unidirectional steering. One of the associated disadvantages with this type of biasing mechanism is that the mechanism is only designed for use with unidirectional steering devices. In other words, the biasing mechanism counters only one direction one movement of the deflectable tip. As procedures become more complex and to permit greater latitude in performing the procedures, it is more desirable to use bidirectional devices in comparison with unidirectional devices. One of skill in the art will appreciate that it is significantly more difficult to provide an active counterforce mechanism for a device having bidirectional steering. One reason is that there is limited room in the housing to position a mechanism which can translate bidirectional movement into one direction on the control mechanism of the deflectable tip.

Therefore, those skilled in the art have recognized the need for a bidirectional mechanism to counter the return to center force generated by the deflected distal end such that the catheter body remains in a deflected state without the continuing input of force from the user while as the same time the force required to initially deflect the distal end is reasonable.

SUMMARY OF THE INVENTION

The present invention is directed to an assembly which provides an active handle for use in a steerable surgical instrument having a shaft deflectable in two directions (bidirectional steering). Typically, the surgical instrument includes a handle component which the user manipulates to cause a distal end of the instrument shaft to deflect in one of two directions. The distal end comprises an end tip portion of the shaft which extends outwardly from the handle. A control mechanism in accordance with the invention is preferably disposed within the handle and extends through the shaft for selectively controlling the direction and degree of deflection at the distal end in one of two directions. For example, one exemplary control mechanism uses control or steering wires to selectively deflect the distal end. The active counterforce mechanism according to the present invention is designed to be used in combination with the control mechanism and provides a force which counters the return to center force generated by the deflection of the shaft at the distal end thereof. Optimally, the active counterforce mechanism exactly balances the return to center force across the instrument's deflection range. This results in the user experiencing little if any resistance during the manual manipulation of the control mechanism in either direction. This permits very low forces to be applied in order to deflect the distal end and also permits low forces to be applied in order to help the instrument maintain and "hold" a particular deflection shape once the shaft is deflected. Accordingly, the handle is made to be an active rather than a passive component of the instrument because the handle itself generates a force via the counterforce mechanism to offset the return to center force generated by the deflected shaft as the shaft is deflected in either direction. In addition, the counterforce mechanism produces a variable force in that as the angle of deflection increases and the return to center force increases, the counterforce likewise progressively increases so as to balance the return to center force.

In one exemplary embodiment, the instrument comprises a bidirectional steerable catheter having a slider based control mechanism disposed within a handle housing. The user manipulates a thumb control linked to the slider for longitudinally displacing the slider within the handle housing. This action causes the steering wires or the like to deflect the distal end of the shaft in one of two directions.

According to a first embodiment, the active counterforce mechanism comprises a mechanical mechanism which includes a rotatable bell crank lever operably connected to a biasing element. The biasing element is also connected to the handle housing and the bell crank lever is connected to the slider using several pivotable members. The counterforce mechanism is designed so that when the slider and the shaft are in neutral positions (nondeflected), the counterforce mechanism provides no counterforce because of the absence of any return to center force. As the control mechanism and more specifically, the slider thereof, is manipulated by the user, the pivotable members pivot and cause the rotation of the bell crank lever. This results in the biasing element applying a force to the bell crank lever such that a counterforce is generated which balances the return to center force of the shaft. In other words, when the slider moves in either the proximal or distal directions, the biasing element applies a force to the bell crank lever which further directs the bell crank lever in the respective direction and prevents the bell crank lever from being forcedly rotated in the opposite direction as a result of the return to center force being applied thereto. The user thus is able to easily and continuously deflect the distal end through its deflection range in both directions using the slider and also a given deflection point may be held more easily due to balancing of the forces acting on the handle mechanisms.

In a second embodiment, the active counterforce mechanism comprises a pivotable cross bar assembly in which the biasing element is in the form of a leaf spring. The pivotable cross bar assembly is flexed outwardly in the either the proximal or distal directions depending upon the directional movement of the slider which is connected thereto using another cross bar. The leaf spring applies a force to the pivotable cross bar assembly so as to encourage and facilitate the outward flexing of the assembly though its range of motion. As in the first embodiment, the mechanism provides a counter force which balances the return to center force generated by the shaft as the shaft travels in one of two directions.

In a third embodiment, the active counterforce mechanism includes a roller assembly having a pair of rollers which travel across first and second track members disposed within the handle. The rollers are connected to linear arms of a torsion spring which is itself connected to the slider using a bar member. The torsion spring serves as the biasing element and generates a force which acts to push the rollers apart. The first and second track members are spaced apart from one another and each preferably includes a curved surface such that as the rollers travel to either end thereof, the torsion spring serves to force the rollers further apart from one another. The force of the torsion spring that is exerted on the slider is approximately zero in the neutral position but increases as the slider is moved and the rollers travel along the track members. This mechanism likewise generates a variable force which counters and preferably balances the return to center force as the slider is moved causing bidirectional movement of the deflectable tip.

It will be understood that there are a number of mechanisms that may be used in making an active type handle where the handle itself generates force instead of merely delivering force as in the designs of the conventional passive handles. In contrast, the active counterforce mechanism of the present invention converts the handle into an active component which generates force in response to the return to center force being generated by the bidirectional shaft. As the handle is used to deflect the instrument through its range, the force produced by the counterforce mechanism becomes progressively greater, to counter the return to center force. This provides assistance to the user in deflecting the distal end and in also maintaining or holding the distal end at a given angle of deflection. According to the present invention, the active counterforce mechanism translates slider movement in two directions into a single biasing direction of the biasing element. Advantageously, the active counterforce mechanism is intended for use with bidirectional devices and is designed to be disposed within the existing constraints on the handle housing.

Other features and advantages of the present invention will be apparent from the following detailed description when read in conjunction with the accompanying drawings.

BRIEF DESCRIPTION OF THE DRAWINGS

FIG. 1 is a perspective view of one exemplary steerable surgical instrument implementing an active counterforce mechanism according to the present invention;

FIGS. 2A–C are diagrammatic illustrations of one exemplary control mechanism for use in the present invention showing the control mechanism and an instrument shaft in neutral and first and second deflected positions;

FIG. 3 is a schematic diagram showing how an active counterforce mechanism of the present invention counters a deflection force generated by the instrument shaft;

FIGS. 4A–C are diagrammatic illustrations of one exemplary active counterforce mechanism according to a first embodiment of the present invention showing the mechanism in neutral, proximal, and distal deflection positions, respectively;

DETAILED DESCRIPTION OF THE PREFERRED EMBODIMENTS

Figure 5:
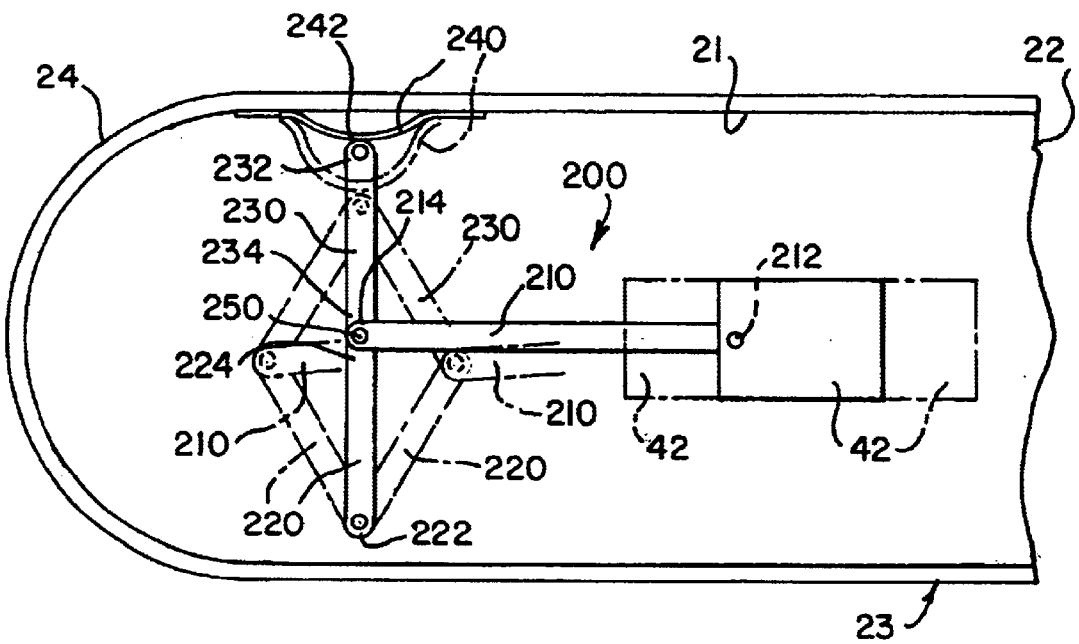
FIG. 5 is a diagrammatic illustration of an active counterforce mechanism according to a second embodiment of the present invention showing the mechanism in neutral, proximal, and distal deflection positions.

Steerable instruments having deflectable tips provide physicians, or operators, an indispensable tool for conveniently accessing the interior of the human body without the level of trauma commonly associated with more invasive surgical techniques. One exemplary steerable instrument is a bidirectional steerable catheter. Referring now to FIGS. 1 through 3C. As shown by example in FIG. 1, a steerable catheter according to one exemplary embodiment of the present invention is generally indicated at 10. The steerable catheter 10 includes an elongated hollow handle 20. The handle 20 has a distal end 22 and an opposing proximal end 24 which is preferably provided with a cable connector 30 for electrical connection to a recording device (not shown) or some other device for capturing electrical signals sensed by electrodes (not shown) commonly used in catheter 10. The manner and details of the construction of the cable connector 30 are not pertinent to the present invention and any number of conventional connectors and assembly techniques may be used.

The interior of the handle 20 defines a compartment 21 for housing a control mechanism, generally indicated at 40, and an active counterforce mechanism, generally indicated at 50. A longitudinal slot 26 formed along the side of the handle 20 defines a linear path for slidable displacement of the control mechanism 40. A narrow flexible shaft 60 projects longitudinally from the distal end 22 of the handle 20 for intravascular insertion. The shaft 60 is typically formed from a plastic material or similar material of a predetermined stiffness and includes one or more longitudinally extending lumens (not shown) for running two or more steering or control wires 70, 80 therethrough. To effect precision steering of a distal end 62 of the shaft 60 during intravascular insertion, the control wires 70, 80 run longitudinally through the catheter shaft lumen and respectively mount to specific distal points inside the shaft 60. The connection points correspond to predetermined directional deflections of the shaft 60 in response to tensile forces placed on a selected control wire 70, 80. The steering wires 70, 80 may comprise stainless steel cables having predetermined tensile strengths, e.g., approximately 15.5 pounds.

FIG. 2 shows one exemplary bidirectional control mechanism 40 for use with the active counterforce mechanism 50 of the present invention. Control mechanism 40 is generally a slider type mechanism and incorporates a slider 42 coupled to proximal ends of the control wires 70, 80. The slider 42 is displaceable along a linear path to place a selected one of the control wires 70, 80 in tension without placing the other of the wires 70, 80 in compression. The slider 42 has a first retaining element 44 for securing the proximal end of the wire 70 and a second retaining element 46 for securing the proximal end of the wire 80. The first retaining element 44 is spaced apart from the second retaining element 46 and in the illustrated embodiment, the first retaining element 44 is located near one end of the slider 42 and the second retaining element 46 is located near the other end of the slider 42. The first and second retaining elements 44, 46 comprise any number of members so long as the elements 44, 46 are movable so that the attached wire 70, 80 may be freely extended and retracted relative to the slider 42 as the slider 42 moves longitudinally within the handle 20 as will be described in greater detail hereinafter.

The slider 42 also preferably includes a pair of spaced apart and longitudinally aligned support pins or the like (not shown) projecting from one side of the slider 42. These support pins are complementally formed so as to slidably engage the handle slot 26. A thumb control 48 mounts to the support pins to prevent the slider 42 from disengaging from the slot 26 and responds to manually applied forces to actuate the control mechanism 40 linearly along the slot path 26. The handle 20 also includes a pulley mechanism 90 which is coupled to the slider 42 via the control wire 70. The pulley mechanism 90 includes a rotatable pulley 92 to redirect the force applied by the slider 42 to the control wire 70. The pulley 92 preferably includes a peripheral groove (not shown) and is rotatably carried by an axle 94 mounted within the handle 20 towards the distal end 22 thereof.

The assembly of the control mechanism 40 comprises fairly straightforward techniques well known to those skilled in the art. Generally, with the respective control wires 70, 80 already anchored to the distal end 62 of the shaft 60, the proximal ends of the wires 70, 80 are measured and trimmed to different lengths to accommodate the pulley 92. Accordingly, the wire 70 is routed around the pulley groove and connects to the first retaining member 44. Control wire 80 is coupled to the slider 42 by connection with the second retaining member 46.

The control mechanism 40 generally works by manual manipulation thereof and more specifically, by manually manipulating the slider 42 so that the distal end 62 of the shaft 60 deflects in a desired direction. By sliding the thumb control 48 forward and rearward, the distal end 62 will be deflected in a corresponding desired direction. For example, an initial rearward force applied to the thumb control 48 linearly displaces the slider 42 towards the proximal end 24 of the handle 20 and causes the slider 42 and pulley mechanism 90 to pull the control wire 70 in the same linear direction, placing a tensile force on the control wire 70 and resulting in a directional deflection of the catheter shaft 60 and more specifically, the distal end 62 thereof. This orientation is illustrated in FIG. 2B, which shows the distal end 62 deflected in a first direction.

To deflect the distal end 62 in an opposite second direction, the slider 42 is moved forward by applying a forward force to the thumb control 48. If the slider 42 is initially positioned in the rearward position shown in FIG. 2B with the distal end 62 of the shaft 60 being deflected in the first direction, the movement of the slider 42 in the forward direction causes the distal end 62 to first straighten out and then continued movement of the slider 42 results in the distal end 62 being deflected in an opposing second deflection direction. This causes the slider 42 and pulley mechanism 90 to pull the control wire 80 in the same linear direction, placing a tensile force on the control wire 80 and resulting in a direction deflection of the distal end 62 in the second deflection direction as shown in FIG. 2C. One of skill in the art will understand that there are a number of different types of bidirectional control mechanisms that may be used and the aforementioned control mechanism 40 is merely exemplary in nature and does not serve to limit the scope of the present invention.

Depending upon the precise control mechanism 40 used and the type of material used to form the catheter shaft 60, the level of force needed to be applied by the user to the control mechanism 40 to deflect the distal end 62 will vary. For example, as the stiffness of the material used to form the catheter shaft 60 increases, more force is required to bend or deflect the distal end 62 of the catheter shaft 60. In addition, the user will have to overcome the friction or drag present in the control mechanism 40 in order to move the slider 42 to cause the respective control wire 70, 80 to be pulled to achieve the desired deflection of the distal end 62. As previously mentioned, when the distal end 62 is positioned in either of the deflected positions shown in FIGS. 2B and 2C, a force ("the return to center force") is generated that tends to drive the distal end 62 back to its straightened orientation shown in FIG. 2A. This force also tends to drive the slider 42 back to its initial neutral position shown in FIG. 2A. Thus in conventional devices, if the user releases the thumb control 48, the return to center force will cause the straightening of the distal end 62. The present invention overcomes this associated disadvantages of the conventional designs by providing an active counterforce handle 20 using the counterforce mechanism 50.

Now referring to FIG. 3 in which a schematic diagram illustrating the active counterforce mechanism 50 of the present invention is provided. The active counterforce mechanism 50 is designed to counter the deflection force generated when the control mechanism 40 (FIG. 1) is manipulated to cause the catheter shaft 60 (FIG. 1) to deflect in either the first or second directions. FIG. 3 illustrates a deflection force curve for a $tip_0$ and a $tip_1$. $Tip_0$ is in the form of a delfectable shaft which is of a first stiffness and $tip_1$ is in the form of a deflectable shaft which is of a second stiffness, where the first stiffness is greater than the second stiffness. For purpose of illustration, the $tip_0$ is referred to as a "stiff" shaft, while the $tip_1$ is referred to as a "soft" shaft. The curve $tip_0$ shows that as the degree of deflection of $tip_0$ is continuously increased, e.g., by continued movement of control mechanism 40 in either the first or second direction, the amount of force required to deflect the $tip_0$ increases in a nonlinear manner. In other words, further slight deflection movement of the $tip_0$ at the end of its range of deflection requires greater and greater applied force by the user to achieve such deflection. Because $tip_1$ is formed of a less stiff material, the curve $tip_1$ illustrates that less force is required to be applied to the $tip_1$ in order to deflect the shaft over its range of deflection. It will be appreciated that the deflection curves represent the force required over a range of deflection degrees to deflect to the shaft in either the first or second directions.

FIG. 3 also illustrates how the active counterforce mechanism 50 (FIGS. 4A–4C) of the present invention counters the return to center force generated by the catheter shaft 60 (FIG. 1) as the shaft 60 is deflected in either the first or second directions. Without the active counterforce mechanism 50 of the present invention, the shaft 60 would return to a non-deflected condition because of the return to center force generated by deflecting the shaft 60. FIG. 3 shows two active counterforce curves which counter corresponding deflection curves. More specifically, an active counterforce curve $ACF_0$ corresponds to the curve $tip_0$ and an active counterforce curve $ACF_1$ corresponds to the curve $tip_1$. Because the active counterforce mechanism 50 is designed to counter the return to center force generated by the shaft 60 over its range od deflection, the active counterforce curve is preferably a mirror image of the deflection curve so that the two forces preferably negate one another. This is shown in FIG. 3 and it will be understood that the active counterforce mechanism 50 is designed to counter any return to center force which is generated by the shaft 60. Thus, the deflection curves shown are merely exemplary in nature and it will be appreciated that the active counterforce mechanism 50 counters the return to center force generated by a shaft having a representative deflection curve.

Now referring to FIGS. 1 and 4A–4C. In accordance with one preferred embodiment of the invention, the active counterforce attributes of the handle 20 are provided by integrating the active counterforce mechanism 50 into the handle 20 in operative combination with the control mechanism 40. FIGS. 4A–4C show the active bidirectional counterforce mechanism 50 according to a first embodiment. Generally, the active bidirectional counterforce mechanism 50 is designed to provide a force to counter the return to center force generated by the catheter shaft 60 as the catheter shaft 60 is deflected in either the first or second directions. This will accordingly assist the user in deflecting the distal end 62 of the catheter shaft 60 over the deflection range of the distal end 62. Optimally, the active counterforce mechanism 50 exactly balances the return to center force from the catheter shaft 60 across its range of motion in the first and second directions resulting in the user experiencing minimal resistance during the manual manipulation of the slider 42 of the control mechanism 40. Even when the balance is only approximated, the active counterforce mechanism 50 permits very low forces to be used by an operator to deflect the distal end 62 and such low forces could therefore also be used to help the operator maintain and "hold" a particular deflection shape once the shaft 60 is deflected. It will be appreciated that the active counterforce mechanism 60 is designed to produce no force when the catheter 10 is in its neutral position shown in FIG. 2A. As the handle 20 is used to deflect the catheter 10 through its deflection range, the counterforce produced by mechanism 50 becomes progressively greater to counter the return to center force which likewise become progressively greater through the deflection range. Advantageously and in accordance with the present invention, the handle 20 is an active component of the catheter 10. In other words, the handle 20 itself generates a force via the active counterforce mechanism 50 and therefore comprises an active type handle for use with bidirectional steering mechanisms in comparison with the passive designs of the conventional handles.

In the first embodiment, the counterforce mechanism 50 comprises a spring/crank mechanism for producing an active variable counterforce as the user manually manipulates the handle 20 through its range of motion. The counterforce mechanism 50 includes a traverse bar member 100, a cam bar 110, a link arm 120, a bell crank lever 130, and a biasing element 150. The traverse bar member 100 includes a distal end 102 and an opposing proximal end 104. The distal end 102 is coupled to the slider 42 so that longitudinal movement of the slider 42 along the length of the handle 20 causes the traverse bar member 100 to likewise move in a generally longitudinal direction within the compartment 21 of the handle 20. The proximal end 104 of the traverse bar member 100 is pivotally mounted within the compartment 21 and serves as a pivotal connection between the traverse bar member 100 and the cam bar 110.

The cam bar 110 has a first end 112 and an opposing second end 114. In the neutral position shown in FIG. 4A, the cam bar 110 is disposed between outer walls 27 of the housing 23 and assumes a generally latitudinal orientation within the housing 23 of the handle 20. The first end 112 is pivotally connected to the proximal end 104 of the traverse bar member 100 and the second end 114 is pivotally mounted to the housing 23. The pivot connections of the first end 112 to the traverse bar member 100 and the second end 114 to the housing 23 may be done using any number of conventional techniques including using pins (not shown) which serve to provide the desired pivot connections. In this instance, the pins are mounted to the housing 23 and the respective members pivot about the pins.

The link arm 120 has a distal end 122 and an opposing proximal end 124. The distal end 122 is pivotally connected to the cam bar 110 and more specifically, in the illustrated embodiment, the distal end 122 is pivotally connected to a central location of the cam bar 110 between the ends 112, 114. In the neutral position, the link arm 120 is generally perpendicular to the cam bar 110 and the pivotable connection therebetween causes the link arm 120 to pivot as the cam bar 110 pivots about its second end 114, as will be described in greater detail hereinafter. In this neutral position, the link arm 120 is longitudinally disposed within the compartment 21 with the link arm 120 being generally parallel to the outer walls 27 of the housing 23. The proximal end 124 is pivotally connected to the bell crank lever 130. The bell crank lever 130 includes a first arm 132 which includes a first aperture 134 to receive the proximal end 124 in a pivotable manner. For example, a pin or the like (not shown) may be disposed through the first aperture 134 and an opening formed in the proximal end 124 so that the two components may pivot about this pin relative to one another. The bell crank lever 130 also includes a second arm 136 which similarly has a second aperture 138 formed therethrough. Between the first and second arms 134, 136, a third aperture 140 is formed. As is known, a bell crank type lever, such as lever 130, has an "L-shape" and is designed to pivot about the third aperture 140. For example, a pin or the like may be disposed within the third aperture 140 to provide a pivot point for the bell crank lever 130 to pivot about. In the neutral position shown in FIG. 4A, the bell crank lever 130 rests in a center of its range of motion and thus, the bell crank lever 130 does not generate a force on either of the members attached thereto. More specifically in the neutral position, the bell crank lever 130 exerts a net force of zero on the link arm 120.

The biasing element 150, or other compressible member which can store energy, has a distal end 152 and an opposing proximal end 154 attached to the housing 23 of the handle 20. In one exemplary embodiment, the biasing element 150 comprises a compression spring. More specifically and according to the illustrated embodiment, the proximal end 154 of the biasing element 150 is attached to the proximal end 24 of the handle 20. The distal end 152 of the biasing element 150 is connected to the second arm 136 at the second aperture 138 and the biasing element 150 applies a distally directed biasing force to the bell crank lever 130. The force applied by the biasing element 150 on the bell crank lever 130 is indicated in FIGS. 4A–4C by the directional arrow F. One exemplary compression spring 150 may be formed of stainless steel wire or other suitable wire material. The traverse arm member 100, the cam bar 110, the link arm 120, and bell crank lever 130 may be formed of any number of suitable materials. Preferably, these members are formed of a metal.

The operation of the counterforce mechanism 50 will now be described with reference to FIG. 4B which illustrates a first slider position when the slider 42 has been moved in the proximal direction. As the slider 42 is moved proximally, the traverse arm member 100 is likewise directed in the proximal direction causing the proximal end 104 of the traverse arm member 100 to direct the first end 112 of the cam bar 110 in a direction toward the proximal end 24 of the handle 20. In other words, the cam bar 110 pivots at the second end 114 thereof and in this instance the cam bar 110 pivots in a generally clockwise direction. Because the distal end 122 of the link arm 120 is pivotally connected to the cam bar 110, movement of the cam bar 110 causes movement of the link arm 120. In this case, the link arm 120 moves in a proximal direction towards the proximal end 24 of the handle 20. In response to the movement of the link arm 120, the bell crank lever 130 rotates about the third aperture 140 in a generally counterclockwise direction. In accordance with the present invention, as soon as the bell crank lever 130 is rotated from the neutral position, the force applied by the biasing element 150 is designed to supplement the rotation of the bell crank lever 130 so that the bell crank lever 130 is forced to the end of its range. In other words, once the bell crank lever 130 begins to rotate away from its neutral position, the force generated by the biasing element 150 on the bell crank lever 130 causes the bell crank lever 130 to quickly move to one end of its range of motion.

One of skill will appreciate that the active counterforce mechanism 40 and more specifically, the biasing element 150, is designed to apply a force on the control mechanism 40 which generally counters the return to center force generated by the catheter shaft 60 at the distal end 62 as the end 62 is deflected in one direction. For example, as the user moves the slider 42 in the proximal direction, the distal end 62 of the shaft 60 is deflected due to the manipulation of the control wires 70, 80. The continued movement of the slider 42 increases the return to center force being generated at the distal end 62. Without the active counterforce mechanism 50 of the present invention, the slider 42 attempts to return to the neutral position by moving in the distal direction to release this built-up force. According to the present invention, the active counterforce mechanism 50 provides a force which counters the return to center force of the catheter shaft 60 as the slider 42 moves in the proximal direction.

The active counterforce mechanism 50 therefore assists the user in deflecting the distal end 62 by eliminating or substantially reducing the difficulties experienced by the user in having to overcome the catheter force in order to effectuate further deflection of the distal end 62. This results because the active counterforce mechanism 50 actually substantially balances or offsets the catheter deflection force over its range of motion. Preferably, the counterforce curve associated with the active counterforce mechanism 40 mirrors the catheter force curve associated with the particular catheter shaft 60. Depending upon the construction of the catheter shaft 60, the catheter force curve will vary. For example, when a stiffer material is used to form the catheter shaft 60, the values of the catheter force curve will be greater because more force is required to further deflect the distal end 62. The required force needed to achieve the further deflection of the distal end 62 progressively increases as the distal end 62 is progressively deflected.

More specifically, the biasing element 150 applies a force to the bell crank lever 130 the range of motion of the bell crank lever 130 so as to progressively direct the bell crank lever 130 in the direction of rotation. In this instance when the slider 42 is moved in the proximal direction, the biasing element 150 applies a progressive force on the bell crank lever 130 to cause it to continue to move according to its full range of motion in the counterclockwise direction.

During movement of the slider 42 in the proximal direction, the the bell crank lever 130 exerts a force which pulls the link arm 120 from center. Because the variable force provided by the active counterforce mechanism 50 preferably balances the catheter force, little applied force is needed to help the catheter 10 maintain or "hold" a particular shape once deflected. In an optimum situation, when the user removes his/her hand from the handle 20 and more specifically from the thumb control 48, the slider 42 rests in the position it was in just prior to removing the hand. In any event, only a slight force applied to the control mechanism 40 is needed to maintain the catheter 10 in the deflected position. This is extremely desirable because it is very convenient for the user to be able to release or apply only a slight force on the thumb control 48 for maintaining the distal end 62 in the deflected position.

It will also be appreciated that the force balancing effect provided by the active counterforce mechanism 50 makes using the steerable instrument 10 easier because the user experiences little resistance during the progressive deflection of the distal end 62. This permits very low forces to be used to deflect the distal end 62. Many users have difficulty using conventional devices because the force required to deflect the catheter may become too great or inconvenient for many users, especially for incremental deflection to an already deflected tip. The active counterforce mechanism 50 of the present invention, however, overcomes this deficiency by effectively offsetting the progressively increasing catheter force.

It will be appreciated that the aforementioned benefits are likewise realized when the user moves the slider 42 in the distal direction. When the slider 42 is moved in the distal direction from the neutral position as shown in FIG. 4C, the traverse bar member 100 is pulled in the distal direction and the cam bar 110 rotates in a counterclockwise manner about the pivot at the second end 114. This counterclockwise motion of the cam bar 110 causes the link arm 120 to be pulled in the distal direction which results in the bell crank lever 130 rotating in a clockwise manner. The biasing element 150 provides a biasing force to the bell crank lever 130 when it rotates clockwise as when it rotates in the opposite counterclockwise direction. The biasing element 150 thus serves to apply a force to the bell crank lever 130 such that the bell crank lever 130 exerts a force against the control mechanism 40 which effectively balances the catheter force. When the slider 42 is moved in the distal direction, the bell crank lever 130 exerts force pushing the link 120 further from center (neutral). Therefore, the bell crank lever 130 is prevented from rotating in the opposite direction once the catheter force becomes greater than the applied force of the user. By balancing the progressively increasing catheter force, the catheter shaft 60 may be easily further deflected at any point within its intended range of motion by the user applying a slight force in that direction. As soon as that slight force is applied, the counterforce is also increased so that there is generally only a slight or ideally no force indifference during the range of movement. Accordingly, even near the end of the range of motion of the distal end 62, the application of only a slight force causes the distal end 62 to continue to deflect. As used herein, the term "slight force" means a force which is substantially less than the required force required in the absence of the counterforce mechanism 50.

According to the present invention, two directions of motion of the slider 42 are translated into a biasing force applied by the biasing element 150 in one direction which acts to counter the centering force generated by the distal end 62 as it is deflected both distally and proximally. It will be understood that the active counterforce mechanism 50 of the present invention is disposed within the housing 20 so that it cooperates with and coexists with the control mechanism 40. In order to fit both mechanisms 40, 50 within the housing 20, one of the mechanism may be designed to travel around the other within the housing 20.

Now referring to FIG. 5 in which an active counterforce mechanism according to a second embodiment is illustrated and generally indicated at 200. The active counterforce mechanism 200 functions generally in the same way as the counterforce mechanism 50 in that it provides a counterforce which balances the return to center force generated by the catheter shaft 60 (FIG. 1). The active counterforce mechanism 200 includes a main traverse bar 210, a first cross bar 220, a second cross bar 230 and a biasing element 240. In FIG. 5, the active counterforce mechanism 200 is shown in a neutral position by solid lines and is shown in proximal and distal positions by phantom lines.

The main traverse bar 210 has a distal end 212 and an opposing proximal end 214 with the distal end 212 being connected to the slider 42. The proximal end 214 is pivotally connected to the first and second cross bars 220, 230 at a pivot joint 250. More specifically, the first cross bar 220 comprises a lower cross bar and includes a first end 222 pivotally connected to the housing 23 of the handle 20. The first cross bar 220 also includes a second end 224 which is pivotally connected to both the proximal end 214 of the main traverse bar 210 and the second cross bar 230 at the pivot joint 250. The second cross bar 230 itself has a first end 232 and an opposing second end 234. The first end 232 of the second cross bar 230 is pivotally connected to a section 242 of the biasing element 240 near the outer wall 27 of the housing 23. The second end 234 is pivotally connected to both the second end 224 of the first cross bar 220 and the proximal end 214 of the main traverse bar 210 at the pivot joint 250. While the main traverse bar 210 extends longitudinally along a length of the handle 20, the first and second cross bars 220, 230 extend across the compartment 21 between the outer wall 27 of the housing 23. Therefore, in the neutral position, the main traverse bar 210 is generally perpendicular to both the first and second cross bars 220, 230.

In the illustrated embodiment, the biasing element 240 comprises a leaf spring having first and second sections 244, 246 on respective opposing sides of the section 242. The second end 234 is thus pivotally connected to a generally central section 242 along the length of the biasing element 240. The biasing element 240 is connected to the housing 20 at the first and second sections 244, 246 and upon application of a load, the biasing element 240 will deflect and generate a force of its own. One will appreciate that the pivot connections formed between elements may be accomplished using any number of techniques including, but not limited to, using pivot pins.

The operation of the active counterforce mechanism 200 will now be described. In the neutral position, the active counterforce mechanism 200 applies no force upon the control mechanism 40 and more specifically upon the slider 42. In this neutral position, the biasing element 240 is in a retracted position and applies no force to the remaining components of the mechanism 200. The slider 42 and the distal end 62 (FIG. 1) are likewise in neutral, non-deflected positions. When the user desires to deflect the distal end 62, the user will move the slider 42 in either a distal or proximal direction depending upon which direction of deflection is desired at the distal end 62. When the slider 42 is moved in the proximal direction, the main traverse bar 210 is also displaced in the proximal direction toward the proximal end 22 of the handle 20. A force is thus applied by the main traverse bar 210 to the first and second cross bars 220, 230 at the joint junction 250. This force causes the first and second bars 220, 230 to flex outwardly towards the proximal end 22 of the handle 20. Because the first ends 222, 232 and the second ends 224, 234 are pivotally connected, the outward flexing of the first and second cross bars 220, 230 is possible.

As the main traverse bar 210 is continuously directed in the proximal direction, the biasing element 240 begins to deflect and apply a force to the other components of the mechanism 200 due to the movement of the second cross bar 230 and once the resistance of the biasing element 240 is overcome by application of the load. Since the second cross bar 230 is pivotally connected to the biasing element 240, the relative movement therebetween causes the respective deflection of the biasing element 240. In this instance, the progressive driving of the first and second cross bars 220, 230 in the proximal direction causes the progressive compression of the biasing element 240. The biasing element 240 is designed to apply a force to the first and second cross bars 220, 230 which encourages the respective proximal movement thereof. In other words, once the user begins to move the slider 42 and the first and second cross bars 220, 230 begin to flex, the biasing element 240 facilitates the flexing of the first and second cross bars 220, 230 so that these members flex through their range of motion. The outward flexing of the first and second cross bars 210, 220 in the proximal direction is indicated in FIG. 5 by phantom lines.

The biasing element 240 is thus designed to provide a force directing the slider 42 in a respective direction away from the neutral position. Once the biasing element 240 beings to apply a force on the slider 42 through the bars 210, 220, 230, the slider 42 is easily driven through its range of motion without the user encountering increased drag which prevents the user from progressively deflecting the distal end 62 by continued movement of the slider 42. The biasing element 240 thus generates a force which acts as a counterforce to the catheter force generated by the deflection of the catheter shaft 60 (FIG. 1). Just as in the case of the active counterforce mechanism 50, the active counterforce mechanism 200 helps the user fully deflect the distal end 62 with minimal force and also permits the distal end 62 to be maintained in a given deflected position using very little applied force.

In a similar manner, when the slider 42 is moved in a distal direction, the main traverse bar 210 is pulled by the slider 42 in the distal direction causing the first and second cross bars 210, 220 to flex outwardly toward the distal end 22 of the handle 20. The biasing element 240 deflects and accordingly exerts a force which facilitates the slider 42 moving through its complete range of motion toward the distal end 22 of the handle 20. As the user continues to move the slider 42 toward the distal end 22, the biasing element 240 continues to direct a force in the same distal direction by encouraging the continued flexing of the first and second cross bars 210, 220 in the distal direction. The outward flexing of the first and second cross bars 210,220 in the distal direction is indicated in FIG. 5 by phantom lines.

Figure 6:
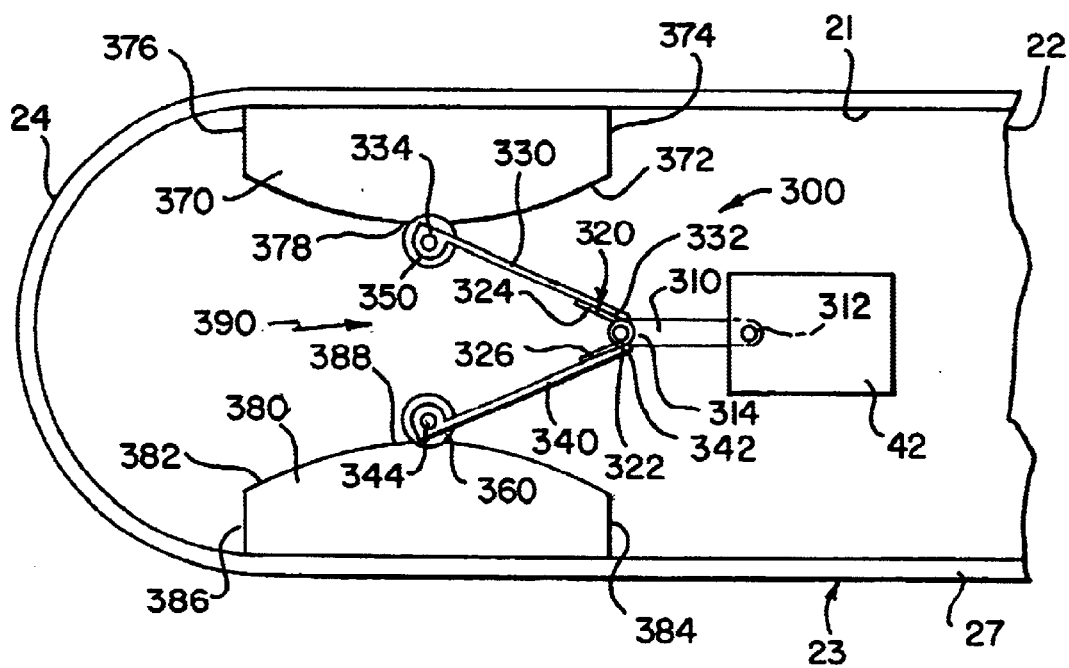
FIG. 6 is a diagrammatic illustration of an active counterforce mechanisms according to a third embodiment of the present invention showing the mechanism in a neutral position.

Now referring to FIG. 6 in which an active counterforce mechanism according to a third embodiment is generally illustrated and indicated at 300. The active counterforce mechanism 300 is disposed within the compartment 21 of the handle 20 and as in the previously-described embodiments, the mechanism 300 provides a force to counter the catheter force generated by the catheter shaft 60 (FIG. 1) during deflection thereof. The counterforce mechanism 300 includes a traverse bar 310, a biasing element 320, first and second roller bars 330, 340, and first and second rollers 350, 360.

More specifically, the traverse bar 310 has a distal end 312 connected to the slider 42 and an opposing proximal end 314 connected to the biasing element 320. The traverse bar 310 generally extends longitudinally within the compartment 21 of the handle 20. In the illustrated embodiment, the biasing element 320 comprises a torsion spring. The torsion spring 320 has a coiled portion 322 and a pair of linear arms 324, 326 extending from the coiled portion 322. The use of a torsion spring, such as torsion spring 320, is well known in the art and will not be described in great detail. The first linear arm 324 connects to the first roller bar 330 at a distal end 332 thereof and the second linear arm 326 connects to the second roller bar 340 at a distal end 342 thereof. A proximal end 334 of the first roller bar 330 connects to the first roller 350 and a proximal end 344 of the second roller bar 340 connects to the second roller 360.

The counterforce mechanism 300 also includes a first track member 370 and an opposing second track member 380. The first and second track members 370, 380 generally comprise members which are disposed within the compartment 21 of the handle 20 to provide a track surface for the first and second rollers 350, 360 to travel therealong. More specifically, the first track member 370 is formed on or mounted to one portion of the outer wall 27 of the handle and the second track member 380 is formed on or mounted to an opposing portion of the outer wall 27. The first track member 370 has a first track surface 372 and the second track member 380 has a second track surface 382 with a gap 390 being formed between the first and second track surfaces 372, 382.

The first track member 370 has a first edge 374 near the slider 42 and an opposing second edge 376 near the proximal end 22 of the handle 20 with the first track surface 372 extending between the first and second edges 374, 376. Similarly, the second track member 380 has a first edge 384 near the slider 42 and an opposing second edge 386 near the proximal end 22 of the handle 20 with the second track surface 382 extending between the first and second edges 384, 386. The specific shape of the first and second track members 370, 380 is not critical so long as the distance between the first track surface 372 and the second track surface 382 is greater at the first and second edges 374, 384, 376, 386 thereof as opposed to a central region 378, 388, respectively. In the illustrated embodiment, each of the first and second track surfaces 372, 382 has a generally convex shape. Accordingly, the distance between the first and second track surfaces 372, 382 progressively increases from the respective central region 378, 388 to the respective first edge 374, 384 and from the central region 378, 388 to the respective second edge 376, 386.

The first and second track surfaces 372, 382 are preferably smooth so as to facilitate travel of the first and second rollers 350, 360 thereon. The first and second rollers 350, 360 have annular shapes so that the rollers 350, 360 freely and smoothly roll along the respective first and second track surfaces 372, 382. In the neutral position shown in FIG. 6, the first and second rollers 350, 360 are slightly spaced apart from one another with the first roller 350 being disposed above the second roller 360. Because the lengths of the first and second linear arms 324, 326 are preferably the same and the lengths of the first and second roller bars 330, 340 are preferably the same, a center axis of each of the first and second rollers 350, 360 is spaced a same distance from the slider 42. Thus, the center axis of each roller 350, 360 is generally aligned with the other.

The operation of the active counterforce mechanism 300 will now be described. In the illustrated neutral position, the first and second rollers 350, 360 are disposed within the respective central region 378, 388 of the first and second track surfaces 372, 382, respectively. In the neutral position, the net force of the biasing element 320 that is exerted on the slider 42 is approximately zero, while the biasing element 320 continuously exerts a force on the first and second rollers 350, 360. Because the tracks 370, 380 are parallel, no force is exerted on the slider 42. Thus in the neutral position, the first and second linear arms 324, 326 apply no force for pushing apart the first and second roller bars 330, 340. If the user moves the slider 42 in the proximal direction toward the proximal end 22 of the handle 20, the first and second rollers 350, 360 begin to roll along the first and second tack surfaces 372, 382. Because the gap 390 between the track surfaces 372, 382 widens in the proximal direction, the angle α between the first and second roller bars 330, 340 increases. Since the first and second roller bars 330, 340 are connected to the first and second linear arms 324, 326, the arms 324, 326 begin to separate further apart from one another. Under these conditions once the active counterforce mechanism 300 begins to move away from the neutral position, the force from the biasing element 320, which is pushing the arms 324, 326 apart, begins to generate a net force on the slider 42 which causes the first and second linear arms 324, 326 to separate from one another. This force causes the first and second rollers 350, 360 to be driven apart from one another; however, the shape of the first and second track members 370, 380 only permit the first and second rollers 350, 360 to be driven further apart as the first and second rollers 350, 360 travel along the first and second track surfaces 372, 382 and the distance increases therebetween.

The force generated by the biasing element 320 progressively increases as the slider 42 moves away from the neutral position and this force facilitates the continued, progressive movement of the slider 42 in the proximal direction over its range of motion. In other words, the biasing element 320 generates the force which counters the return to center force generated at the distal end 62 (FIG. 1) and therefore permits the user to easily move the slider 42 in the proximal direction without experiencing undue difficulties and also permits the distal end 62 to be maintained in the deflected state by exerting only a slight force to the control mechanism 40 (slider 42).

In a similar manner, the movement of the slider 42 in the distal direction, causes the traverse bar 310 to be pulled by the slider 42. This action pulls the first and second rollers 350, 360 along the first and second track surfaces 372, 382 in the distal direction. Once the biasing element 320 is moved from its neutral position, it begins to exert a net force on the slider 42. The curved shape of the first and second track members 370, 380 causes the biasing element 320 to try to "squirt" the first and second rollers 350, 360 out at either the first edges 374, 384 or the second edges 376, 386, thus providing the counterforce needed at the slider 42. The counterforce generated by mechanism 300 is thus variable and balances the return to center force over the deflection range of the distal end 62 (FIG. 1) so that the aforementioned advantages of the present invention are realized. In one exemplary embodiment, the first and second track members 370, 380 are formed of a plastic material and may be either integrally formed as part of the handle housing 23 or may be mounted within the compartment 21 by known techniques.

The present invention thus provides an active handle assembly in which the internal components of the handle itself serve to substantially counter or offset the return to center force generated by the shaft of a bidirectional deflectable shaft instrument. According to the present invention, two directions of motion of the slider 42 are translated into a biasing force applied by the biasing element in a single direction which acts to counter the return to center force as the distal end 62 is deflected in either the proximal or distal directions. It will be understood that the previously described and illustrated embodiments are merely exemplary in nature and a number of other embodiments are possible for a providing a handle which includes a mechanism to actively produce force to counter the forces expected from the instrument. This results in better control and convenience of use of the overall instrument. Advantageously, the use of the active counterforce mechanism of the present invention permits the instrument shaft and distal end to be formed of a material having a greater stiffness. The use of stiffer shafts is desirable in many surgical applications because of certain anatomical benefits provided by the stiffer shafts. When stiffer shafts are used, any unnecessary or unwanted bending of the shaft and more particularly the distal end is reduced or eliminated.

While the invention has been particularly shown and described with reference to the preferred embodiments thereof, it will be understood by those skilled in the art that various changes in form and detail may be made therein without departing from the spirit and scope of the invention.

What is claimed is:

1. A handle assembly for use in an instrument having bidirectional steering and a deflectable shaft, wherein upon being deflected in a first direction, the shaft generates a return force in an opposite second direction, and the shaft whereupon being deflected in the second direction generates a return force in the opposite first direction, the assembly comprising:

a manually positionable control mechanism coupled to the shaft to selectively deflect the shaft in the first and second directions; and a counterforce mechanism operably coupled to the control mechanism and arranged to actively reduce a deflection force needed to continue to deflect the shaft in one of the first and second directions, the counterforce mechanism applying a biasing force to the control mechanism in a direction opposite to the return force once the control mechanism is moved from a neutral position in which the shaft is in a straightened position, the biasing force being about equal to the return force so that the forces effectively offset one another and permit a user to more easily and progressively deflect the shaft.

2. A handle assembly for use in an instrument having bidirectional steering an a deflectable shaft, wherein upon being deflected in a first direction, the shaft generates a return force in an opposite second direction, and the shaft whereupon being deflected in the second direction generates a return force in the opposite first direction, the assembly comprising:

a manually positionable control mechanism coupled to the shaft to selectively deflect the shaft in the first and second directions, the control mechanism including a slider displaceable long a linear path for causing the deflection of the shaft in the first and second directions; and a counterforce mechanism operably coupled to the slider, the counterforce mechanism including a biasing element to bias the slider in a direction opposite to the return force once the slider is moved from a neutral position in which the shaft is in a straightened position, the biasing element providing a variable biasing force to the slider to counter the variable return force generated as the shaft deflects due to movement of the slider from the neutral position to one of the first and second directions, wherein the biasing force is about equal to he return force so that the forces effectively offset one another and permit a user to more easily and progressively deflect the distal end.

3. A handle assembly for use in an instrument having bidirectional steering and a deflectable shaft, wherein upon being deflected in a first direction, the shaft generates a return force in an opposite second direction, and the shaft whereupon being deflected in the second direction generates a return force in the opposite first direction, the assembly comprising:

a manually positionable control mechanism operably connected to the shaft to selectively deflect the shaft in the first and second directions, the control mechanism including a slider displaceable along a linear path for causing the deflection of the shaft in the first and second directions; and a counterforce mechanism operably coupled to the slider, the counterforce mechanism including a biasing element to bias the slider in a direction opposite to the return force once the slider is moved from a neutral position in which the shaft is in a straightened position, the counterforce mechanism including first and second roller members operably connected to the biasing element which is itself operably connected to the slider, the first roller member being disposed on a surface of a first track member and the second roller member being disposed on a surface of a second track member spaced apart from the first track member, the biasing element acting to bias apart the first and second rollers from one another as the rollers travel along the surfaces of the first and second track members resulting in the slider being biased in a direction opposite to the return force.

4. The handle assembly of claim 3, wherein each surface of the first and second track members has a convex shape, the first and second track members being spaced apart from one another in opposing fashion with the first and second roller being disposed therebetween.

5. The handle asssembly of claim 3, wherein the distance between the surfaces of the first and second track members increases toward edges of the first and second track members such that as the slider is linearly displaced, the rollers are linearly displaced in the same direction and further separated apart due to the biasing force.

6. The handle assembly of claim 3, wherein the biasing element comprises a torsion spring.

7. The handle assembly of claim 3, wherein the counterforce mechanism includes a traverse bar extending from the slider and connecting to the biasing element which comprises a torsion spring having first and second linear arms, the first linear arm being connected to a first roller bar which connects to the first roller, the second linear arm being connected to a second roller bar which connects the second roller, the biasing force of the element acting to forcibly separate the first and second linear arms as the slider is linearly displaced.

* * * * *